Shapiro

[11] Patent Number: 4,917,719
[45] Date of Patent: Apr. 17, 1990

[54] HERBICIDAL ISOTHIAZOLE DERIVATIVES

[75] Inventor: Rafael Shapiro, Wilmington, Del.

[73] Assignee: E. I. Du Pont de Nemours and Company, Wilmington, Del.

[21] Appl. No.: 853,227

[22] Filed: Apr. 17, 1986

Related U.S. Application Data

[60] Division of Ser. No. 639,942, Aug. 13, 1984, Pat. No. 4,604,130, which is a continuation-in-part of Ser. No. 478,146, Mar. 30, 1983, abandoned.

[51] Int. Cl.$^4$ .................. C07D 417/12; A01N 43/66
[52] U.S. Cl. ........................................ 71/90; 71/93; 544/212
[58] Field of Search ................ 71/93, 90; 544/212

[56] References Cited

U.S. PATENT DOCUMENTS

| | | | |
|---|---|---|---|
| 4,127,405 | 11/1978 | Levitt | 544/211 |
| 4,169,719 | 10/1979 | Levitt | 544/320 |
| 4,368,067 | 1/1983 | Budzinski et al. | 544/212 |
| 4,398,939 | 8/1983 | Levitt | 544/212 |
| 4,441,910 | 4/1984 | Shapiro | 544/212 |
| 4,481,029 | 11/1984 | Levitt | 544/212 |

FOREIGN PATENT DOCUMENTS

| | | |
|---|---|---|
| 95925 | 12/1983 | European Pat. Off. |
| 57-31377 | 9/1983 | Japan . |
| 57-45972 | 9/1983 | Japan . |
| 58-148879 | 9/1983 | Japan . |
| 58-162587 | 9/1983 | Japan . |
| 57-123263 | 1/1984 | Japan . |
| 59-137778 | 1/1984 | Japan . |
| 59-31775 | 2/1984 | Japan . |
| 57-142069 | 2/1984 | Japan . |
| 59-122488 | 7/1984 | Japan . |
| 57-228261 | 7/1984 | Japan . |
| 83-3850 | 5/1983 | South Africa . |

Primary Examiner—John M. Ford

[57] ABSTRACT

Certain N-[(heterocyclic)aminocarbonyl]isothiazolesulfonamides, such as methyl 4-[[(4-methoxy-6-methylpyrimidin-2-yl)aminocarbonyl]aminosulfonyl]-3-isothiazolecarboxylate, are useful as herbicides and/or plant growth regulants.

6 Claims, No Drawings

HERBICIDAL ISOTHIAZOLE DERIVATIVES

RELATED APPLICATION

This application is a divisional of my copending application U.S. Ser. No. 639,942, filed Aug. 13, 1984, now U.S. Pat. No. 4,604,130, which in turn is a continuation-in-part of my application U.S. Ser. No. 478,146, filed Mar. 30, 1983, now abandoned.

BACKGROUND OF THE INVENTION

This invention relates to novel N-[(heterocyclic-)aminocarbonyl]isothiazolesulfonamides where the heterocycle is pyrimidine or triazine, to herbicidal compositions containing them and to methods of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

A number of different types of N-[(heterocyclic-)aminocarbonyl]arylsulfonamides are known as herbicides. Two of the first patents to issue on such compounds are U.S. Pat. Nos. 4,169,719 and 4,127,405, issued on Oct. 2, 1979 and Nov. 28, 1978, respectively. These patents disclose compounds of the general formula

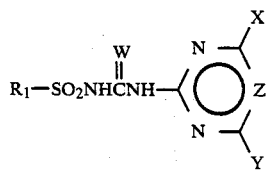

where
W can be O or S,
Z can be N or CH, and
R is optionally substituted benzene, optionally substituted thiophene, optionally substituted furan or naphthalene.

Later publications have disclosed similar compounds where $R_1$ is a thiophene or pyrrole. See, for example, U.S. Pat. No. 4,398,939, issued Aug. 16, 1983, U.S. Pat. No. 4,441,910, issued Apr. 10, 1984 and European Patent Publication (EP-A) No. 30,142, published Jun. 10, 1981 which disclose herbicidal thiophene sulfonamides and U.S. Pat. No. 4,368,067, issued Jan. 11, 1983 which discloses herbicidal pyrrole sulfonamides. [Herbicidal thiazole and pyrazole sulfonamides are disclosed in U.S.S.N. 609,695, filed May 14, 1984 and U.S.S.N. 486,092, filed Apr. 25, 1983, respectively.]

European Patent Publication (EP-A) No. 96,003, published Nov. 28, 1983, discloses herbicidal sulfonylureas of general formula

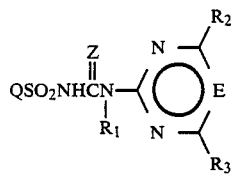

wherein
$R_1$ is H or $C_1$–$C_5$ alkyl;
$R_2$ and $R_3$ independently of one another are each H, $C_1$–$C_5$ alkyl, $C_1$–$C_5$ alkoxy, $C_1$–$C_5$ alkylthio, $C_1$–$C_5$ haloalkyl, halogen, $C_1$–$C_5$ haloalkoxy, $C_1$–$C_5$ haloalkylthio, $C_1$–$C_5$ alkylamino, di-$C_1$–$C_4$ alkylamino or an alkoxyalkyl group of alkoxyalkoxy group each having a maximum of 6 carbon atoms;
Z is O or S;
E is CH or N; and
Q is an unsubstituted or substituted, five-membered, heterocyclic radical which is bound by way of a carbon atom, and which contains 2 or 3 identical or different hetero atoms.

SUMMARY OF THE INVENTION

It has now been found that the novel compounds of Formula I possess herbicidal and/or plant growth regulant utility.

$$QSO_2NHCONHA \qquad I$$

where
Q is

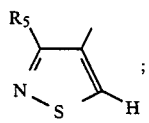

$R_5$ is Cl, $C_1$–$C_3$ alkoxycarbonyl or $C_1$–$C_3$ alkyl;
A is

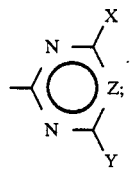

X is $CH_3$, $OCH_3$, $OCF_2H$, $OC_2H_5$, $CH_2OCH_3$, or cyclopropyl;
Y is $CH_3$, $OCH_3$ or $OCF_2H$; and
Z is CH or N;
provided that when either X or Y is $OCF_2H$, then Z is CH; and agriculturally suitable salts thereof.

This invention therefore relates to novel compounds of Formula I, to herbicidal compositions containing them, and to methods of using them to control the growth of undesired vegetation.

Preferred for reasons of their high herbicidal activity, plant growth regulant activity and/or favorable ease of synthesis are the following groups of compounds:
(1) Compounds of Formula I where Z is CH.

(2) Compounds of Formula I where Z is CH and $R_5$ is $CO_2CH_3$ or Cl.

The following compounds are specifically preferred for reasons of their high herbicidal activity, plant growth regulant activity and/or favorable ease of synthesis:

Methyl 4-[[(4-methoxy-6-methylpyrimidin-2-yl)aminocarbonyl]aminosulfonyl]-3-isothiazolecarboxylate, m.p. 128° C.(d);

Methyl 4-[[(4,6-dimethoxypyrimidin-2-yl)aminocarbonyl]aminosulfonyl]-3-isothiazolecarboxylate, m.p. 161° C.(d); and 3-Chloro-N-[(4-methoxy-6-methylpyrimidin-2-yl)aminocarbonyl]-4-isothiazolesulfonamide, m.p. 153°–155° C. (d).

DETAILED DESCRIPTION

Synthesis

The compounds of this invention where Q and A are as previously defined may be prepared, as shown in Equation 1, by reaction of an appropriately substituted sulfonyl isocyanate of Formula II with the appropriate heterocyclic amine of Formula III.

Equation 1

$$QSO_2NCO + H_2NA \longrightarrow I$$
$$\text{II} \quad\quad\quad \text{III}$$

The reaction of Equation 1 is generally carried out by adding a solution of the sulfonyl isocyanate II in an inert solvent, such as methylene chloride or acetonitrile, to a solution or suspension of the heterocyclic amine III in the same solvent. The mixture is stirred from about one to twenty-four hours at temperatures from ambient to the reflux temperature of the solvent. In the some cases, the reaction is exothermic and the compounds of Formula I crystallize from the reaction mixture. When the compounds of Formula I are soluble in the reaction medium, they can be isolated by evaporation of the solvent and trituration with a suitable solvent such as 1-chlorobutane or hexane.

Sulfonyl isocyanates of Formula II, where Q is as previously defined can be prepared, as shown in Equation 2, by reaction of sulfonamides of Formula IV with phosgene in the presence of an alkyl isocyanate, such as butyl isocyanate, in an inert solvent, such as xylene or chlorobenzene, according to the procedure of H. Ulrich and A. A. Y. Sayigh, "New Methods of Preparative Organic Chemistry", Vol. VI, p. 223–241, Academic Press, N. Y. and London, W. Foerst, Ed.

Equation 2

$$QSO_2NH_2 + COCl_2 \xrightarrow{C_4H_9NCO} \text{II}$$
$$\text{IV}$$

Alternatively, the reaction shown in Equation 2 can be carried out in the presence of a catalytic amount of a tertiary amine, such as triethylamine or 1,4-diaza[2.2.2]bicyclooctane, by the procedure described in U.S. Pat. No. 4,379,769.

Alternatively, many compounds of Formula I, where Q and A are as previously defined, but $R_5$ is other than $C_1-C_3$ alkoxycarbonyl, may be prepared by the method described in Equation 3, namely, by reaction of a sulfonamide of Formula IV, where Q is as previously defined but $R_5$ is other than $C_1-C_3$ alkoxycarbonyl, with a heterocyclic carbamate of Formula V in the presence of at least one molar equivalent of trimethylaluminum.

Equation 3

$$\text{IV} + CH_3O\overset{O}{\underset{\|}{C}}NHA \xrightarrow{(CH_3)_3Al} I$$
$$\quad\quad\quad\quad V$$

The reaction of Equation 4 is generally carried out in an inert solvent, such as methylene chloride or toluene, under an inert atmosphere, at temperatures from ambient up to the reflux temperature of the solvent for about 6–96 hours. The product can be isolated by addition of dilute hydrochloric acid to the cooled reaction mixture followed by separation of the organic phase, drying of the solution and evaporation of the solvent. The product can be purified by trituration with, or crystallization from, solvents such as 1-chlorobutane, hexane, ethanol or similar solvents.

Many of the compounds of Formula I, where Q and A are as previously defined, may be prepared by contacting equimolar amounts of a phenylcarbamate of Formula Va with a sulfonamide of Formula IV in the presence of a suitable base as shown in Equation 3A.

Equation 3A $$\text{IV} + C_6H_5O\overset{O}{\underset{\|}{C}}NHA \xrightarrow{DBU} I$$
$$\quad\quad\quad\quad Va$$

The reaction is carried out at 0° to 50° C. in an inert solvent such as acetonitrile for 0.1 to 24 hours in the presence of a base such as 1,8-diazabicyclo[5.4.0]-undec-7-ene (DBU) as taught in EPO Publication No. 44,807. The methyl and phenyl carbamates of Formula V and Va may be prepared by reaction of the heterocyclic amine of Formula III with methyl carbonate or methyl chloroformate or with phenyl carbonate or phenyl chloroformate, respectively, in the presence of a suitable base.

Another procedure for the preparation of many compounds of this invention is by the reaction of a carbamate of Formula VI, where Q is as previously defined, with a heterocyclic amine III by the procedure described in EPO Publication No. 44,807, as shown in Equation 4.

Equation 4

$$QSO_2NHCO_2C_6H_5 + \text{III} \longrightarrow I$$
$$\text{VI}$$

Sulfonamides of Formula IV can be prepared by amination of the corresponding sulfonyl chlorides of Formula VII by methods well known in the art. The intermediate sulfonyl chlorides of Formula VII can be prepared by one of the methods shown in Equation 5.

Equation 5

$$\text{A.} \quad QSCH_2C_6H_5 + Cl_2 \xrightarrow[H_2O]{CH_3CO_2H} QSO_2Cl$$
$$\quad\quad\quad \text{VIII} \quad\quad\quad\quad\quad\quad\quad\quad\quad \text{VII}$$

-continued
Equation 5

B. 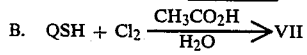 →VII
IX

C. 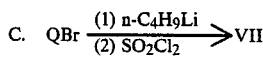 →VII
X

D. QH + ClSO$_3$H ——→VII
XI

E. 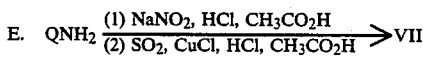 →VII
XII

In Equations 5A and 5B, a solution or a suspension of a benzyl sulfide of Formula VIII or a thiol of Formula IX in aqueous acetic acid is treated with at least three molar equivalents of chlorine at temperatures of about 0° to 15°. The sulfonyl chloride of Formula VII can be isolated by dilution of the reaction mixture with water, followed by either filtration or extraction with an organic solvent such as ether, methylene chloride or 1-chlorobutane.

In Equation 5C, a bromide of Formula X is treated with one molar equivalent of n-butyl lithium, in solvents such as ether, tetrahydrofuran or dimethoxyethane, at temperatures of about −78° to −20°. The intermediate lithioheterocycle is added to an excess of sulfuryl chloride in a solvent such as hexane or ether at temperatures of about −20° to 0°. The sulfonyl chloride of Formula VII can be isolated by addition of water to the reaction mixture, separation of the organic solution, and evaporation of the solvents.

In Equation 5D, a heterocycle of Formula XI is treated with an excess of chlorosulfonic acid at temperatures of about ambient to the boiling point of chlorosulfonic for periods of from several hours to several days. The sulfonyl chlorides of Formula VII can be isolated by pouring the reaction mixture into ice water, and either filtering the product or extracting it into an organic solvent.

In Equation 5E, a heterocyclic amine of Formula XII is diazotized with sodium nitrite in a mixture of water, concentrated hydrochloric acid and acetic acid at temperatures from about −5° to 10°. The resulting diazonium salt is added to a mixture of sulfur dioxide, cuprous or cupric chloride, concentrated hydrochloric acid and acetic acid, and the reaction mixture is stirred at temperatures from about 0° to ambient. The sulfonyl chloride of Formula VII can be isolated by diluting the reaction mixture with water and either filtration or extraction with an organic solvent.

The synthesis of the heterocyclic amines of Formula III has been reviewed in "The Chemistry of Heterocyclic Compounds", a series published by Interscience Publishers. 2-Aminopyrimidines are described by D. J. Brown in "The Pyrimidines" in Vol. XVI of the series; 2-aminotriazines are described by E. M. Smolin and L. Rapoport in "s-Triazines and Derivatives", in Vol. XIII of the series, both of the teachings of which are herein incorporated by reference. Compounds of Formula III where X or Y is OCF$_2$H can be prepared by the methods described in South African Patent Application No. 825,045. Compounds of Formula III where X is cyclopropyl can be prepared by the methods described in South African Patent Application No. 837,434.

Agriculturally suitable salts of compounds of Formula I are also useful herbicides and can be prepared in a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I or II with a suitable acid, e.g., p-toluenesulfonic acid, trichloroacetic acid or the like.

The compounds of this invention are further illustrated by the following examples, wherein temperatures are given in degrees centigrade and parts are by weight unless otherwise indicated.

EXAMPLE 1

3-Chloro-4-isothiazolesulfonamide (IV; R$_5$=Cl)

A mixture of 20 g of 3-chloroisothiazole and 100 ml of chlorosulfonic acid was refluxed 0.5 hour, cooled and heated at 90° overnight, then refluxed for 2 days. The mixture was cooled and poured slowly onto ice. The aqueous mixture was extracted with ether; the organic solution was washed with water and brine, then dried over magnesium sulfate, filtered and the solvent evaporated. The residual oil was dissolved in ether and treated with gaseous ammonia for 1 hour at 10°. The reaction mixture was filtered and the filtrate evaporated. The residual solid was washed with hexane, collected and dried giving 8.2 g of the title sulfonamide, m.p. 110°–116°. IR: 3400 and 3270 cm$^{-1}$ (SO$_2$NH$_2$).

EXAMPLE 2

3-Chloro-4-isothiazolesulfonyl isocyanate (II; R$_5$=Cl)

A mixture of 4.0 g of the sulfonamide, prepared in Example 1, 8.0 ml of butyl isocyanate, 0.1 g of diaza[2.2.2]bicyclooctane and 40 ml of xylene was heated to reflux and treated dropwise with a solution of 2.4 ml of phosgene in 10 ml of xylene. The reaction mixture was refluxed 4 hours, then cooled, and the solvent was evaporated. The residual crude sulfonyl isocyanate (IR-2250 cm$^{-1}$) was dissolved in 50 ml of methylene chloride.

EXAMPLE 3

3-Chloro-N-[(4,6-dimethylpyrimidin-2-yl)aminocarbonyl]-4-isothiazolesulfonamide (I; $R_5$=Cl Z=CH, X=Y=$CH_3$)

A 10 ml portion of the methylene chloride solution of 3-chloro-4-isothiazolesulfonyl isocyanate, prepared in Example 2, was added to 0.2 g of 4.6-dimethyl-2-pyrimidinamine, and the mixture stirred 0.5 hour at ambient temperature. The solvent was evaporated and the residual solid triturated with ether, collected and dried giving 0.5 g of the title compound, m.p. 136°–140°. IR: 1720 and 1700 cm$^{-1}$ (C=O).

NMR (CDCl$_3$): δ 2.5 (s, 6H, CH$_3$), 6.8 (s, 1, pyrimidine CH) and 9.5 (s, 1H, isothiazole CH).

EXAMPLE 4

Methyl 4-(aminosulfonyl)-3-isothiazolecarboxylate (IV; $R_5$=$CO_2CH_3$)

A. A suspension of 52.0 g of 4-amino-3-isothiazolecarboxylic acid hydrochloride [prepared by the method of K. Gewald and P. Billman, *Liebigs Ann.* 1542 (1979)] in 300 ml methanol was cooled in an ice-bath and 10 ml of thionyl chloride was added dropwise. The reaction mixture was refluxed 3 hours, cooled and the solvent evaporated. The residual solid was collected, washed with ether and dried giving 47.5 g of methyl 4-amino-3-isothiazolecarboxylate hydrochloride, m.p. 170°(d).

B. A suspension of 38 g of the amine hydrochloride, prepared in Part A, in 100 ml acetic acid was cooled to 15° and diluted with 100 ml of concentrated hydrochloric acid. The mixture was cooled to 0° and a solution of 16 g of sodium nitrite in 40 ml water was added dropwise over 30 minutes. The reaction mixture was stirred 1 hour at −5° to 0° then added portionwise to a stirred mixture of 5 g of cuprous chloride, 5 ml of concentrated hydrochloric acid, 40 ml of sulfur dioxide and 200 ml of acetic acid at 0°. After 1 hour at approximately 5°, when gas evolution had ceased, the reaction mixture was poured into 400 ml of ice-water and allowed to stand 30 minutes. The resulting solid was collected and dried giving 25.0 g of methyl 4-(chlorosulfonyl)-3-isothiazolecarboxylate, m.p. 42°–46°.

C. A solution of 21.4 g of the sulfonyl chloride, prepared in Part B, in 200 ml of tetrahydrofuran was cooled to −70° and treated with 5.5 ml of liquid ammonia. The reaction mixture was allowed to warm to −20° to −10°, stirred 15 minutes, and adjusted to pH 7 with concentrated hydrochloric acid. The resulting solid was collected, washed with tetrahydrofuran and dried giving 18.8 g of the title sulfonamide, m.p. 107°–113°.

NMR (CDCl$_3$/DMSO-d$_6$): δ 4.0 (s, 3H, OCH$_3$), 7.0 (broad s, 2H, SO$_2$N$_2$) and 9.3 (s, 1H, isothiazole CH).

EXAMPLE 5

3-(Methoxycarbonyl)-4-isothiazolesulfonyl isocyanate (II; $R_5$=$CO_2CH_3$)

A mixture of 9.0 g of the sulfonamide prepared in Example 4, 6 ml of butyl isocyanate, 0.2 g of diaza[2.2.2]bicyclooctane and 150 ml of xylene was heated to 125°, and a solution of 4 ml of phosgene in 6 ml of xylene was added dropwise. A small amount of tar had formed when addition was complete. A 0.2 g portion of diaza[2.2.2]bicyclooctane was added, and the mixture was refluxed 2 hours. The reaction mixture was cooled, decanted from the tar, and the solvent evaporated giving the sulfonyl isocyanate as an orange oil. The crude sulfonyl isocyanate was dissolved in 50 ml of methylene chloride for reaction with heterocyclic amines. IR: 2240 cm$^{-1}$ (SO$_2$NCO) and 1735 cm$^{-1}$ (C=O).

EXAMPLE 6

Methyl 4-[[(4,6-dimethylpyrimidin-2-yl)aminocarbonyl]aminosulfonyl]-3-isothiazolecarboxylate (I; $R_5$=$CO_2H_3$, Z=CH, X=Y=$CH_3$)

To a solution of 0.5 g of 4.6-dimethyl-2-pyrimidinamine in 10 ml methylene chloride was added 10 ml of the methylene chloride solution of the sulfonyl isocyanate prepared in Example 4, and the reaction mixture was stirred 15 minutes. The solvent was evaporated, and the residue was triturated with a mixture of methylene chloride and ether. The solid was collected and dried giving 1.0 g of the title compound, m.p. 167° (d). IR: 1735, 1720 and 1700 cm$^{-1}$ (C=O).

NMR (CDCl$_3$/DMSO-d$_6$): δ 2.4 (s, 6H, CH$_3$), 3.9 (s, 3H, OCH$_3$), 6.9 (s, 1H, pyrimidine CH), 9.8 (s, 1H, isothiazole CH) and 11.8 (broad s, 1H, NH).

By the methods described in Examples 1–6, or modifications thereof, the compounds of Table I may be prepared.

TABLE I

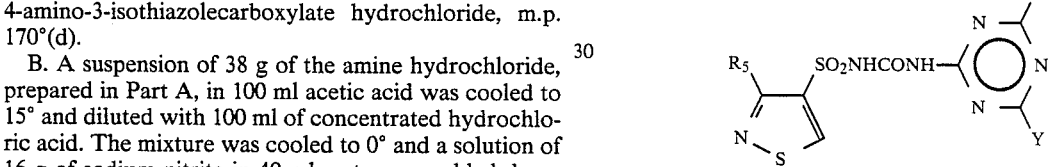

| $R_5$ | X | Y | Z | m.p. (°C.) |
|---|---|---|---|---|
| Cl | CH$_3$ | CH$_3$ | CH | 136–140°(d) |
| Cl | OCH$_3$ | CH$_3$ | CH | 153–155°(d) |
| Cl | OCH$_3$ | OCH$_3$ | CH | 145–150° |
| Cl | CH$_2$OCH$_3$ | CH$_3$ | CH | |
| Cl | CH$_3$ | OCH$_3$ | N | 156–160°(d) |
| Cl | OCH$_3$ | OCH$_3$ | N | 163–167°(d) |
| Cl | CH$_3$ | CH$_3$ | N | |
| Cl | CH$_2$OCH$_3$ | OCH$_3$ | N | |
| CH$_3$O$_2$C | CH$_3$ | CH$_3$ | CH | 167°(d) |
| CH$_3$O$_2$C | OCH$_3$ | CH$_3$ | CH | 120°(d) |
| CH$_3$O$_2$C | OCH$_3$ | OCH$_3$ | CH | 161°(d) |
| CH$_3$O$_2$C | OCH$_3$ | CH$_3$ | N | 181°(d) |
| CH$_3$O$_2$C | OCH$_3$ | OCH$_3$ | N | 180°(d) |
| CH$_3$O$_2$C | CH$_3$ | CH$_3$ | N | |
| C$_2$H$_5$O$_2$C | CH$_3$ | OCH$_3$ | CH | |
| C$_2$H$_5$O$_2$C | OCH$_3$ | CH$_3$ | CH | |
| C$_2$H$_5$O$_2$C | OCH$_3$ | OCH$_3$ | CH | |
| C$_3$H$_7$O$_2$C | OCH$_3$ | OCH$_3$ | CH | |
| CH$_3$ | CH$_3$ | CH$_3$ | CH | |
| CH$_3$ | CH$_3$ | OCH$_3$ | CH | |
| CH$_3$ | OCH$_3$ | OCH$_3$ | CH | |
| CH$_3$ | CH$_3$ | OCH$_3$ | N | |
| CH$_3$ | OCH$_3$ | OCH$_3$ | N | |
| CH$_3$ | CH$_3$ | CH$_3$ | N | |
| C$_2$H$_5$ | CH$_3$ | OCH$_3$ | N | |
| Cl | OCF$_2$H | CH$_3$ | CH | |
| C$_2$H$_5$ | OCH$_3$ | OCH$_3$ | N | |
| C$_2$H$_5$ | OCH$_3$ | OCH$_3$ | CH | |
| C$_3$H$_7$ | CH$_3$ | OCH$_3$ | CH | |
| C$_3$H$_7$ | CH$_3$ | CH$_3$ | CH | |
| C$_3$H$_7$ | OCH$_3$ | OCH$_3$ | CH | |
| Cl | cyclopropyl | CH$_3$ | CH | |
| Cl | cyclopropyl | OCH$_3$ | N | |
| CH$_3$O$_2$C | cyclopropyl | OCH$_3$ | N | |
| CH$_3$O$_2$C | cyclopropyl | CH$_3$ | CH | |
| CH$_3$ | cyclopropyl | CH$_3$ | CH | |
| CH$_3$ | cyclopropyl | OCH$_3$ | N | |
| Cl | OC$_2$H$_5$ | CH$_3$ | N | |
| Cl | OC$_2$H$_5$ | CH$_3$ | CH | |
| CH$_3$O$_2$C | OC$_2$H$_5$ | CH$_3$ | N | |

TABLE I-continued

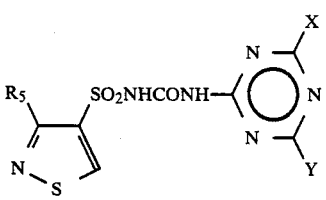

| R5 | X | Y | Z | m.p. (°C.) |
|---|---|---|---|---|
| CH3O2C | OC2H5 | CH3 | CH | |
| CH3 | OC2H5 | CH3 | N | |
| CH3 | OC2H5 | CH3 | CH | |
| i-C3H7 | OCH3 | OCH3 | CH | |
| i-C3H7 | OCH3 | CH3 | N | |
| CH3O2C | OCF2H | OCF2H | CH | |
| CH3O2C | CH3 | OCF2H | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% weight of active ingredient(s) and at least one of (a) about 0.1% to 20% sufactant(s) and (b) about 1% to 99.9% solid or liquid inert diluent(s). More specifically, they will contain these ingredients in the following approximate proportions:

TABLE II

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of sufactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0°. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon performed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, N.Y., 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc., N.Y., 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 7

| Wettable Powder | |
|---|---|
| Methyl 4-[[(4-methoxy 6-methylpyrimidin-2-yl)-aminocarbonyl]aminosulfonyl]-3-isothiazole-carboxylate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| Methyl 4-[[(4,6-dimethoxypyrimidin-2-yl)aminocarbonyl]-aminosulfonyl]-3-isothiazolecarboxylate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 10

| Extruded Pellet | |
|---|---|
| Methyl 4-[[(4,6-dimethoxypyrimidin-2-yl)aminocarbonyl]-aminosulfonyl]-3-isothiazolecarboxylate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Low Strength Granule | |
|---|---|
| Methyl 4-[[(4-methoxy-6-methylpyrimidin-2-yl)-aminocarbonyl]aminosulfonyl]-3-isothiazole-carboxylate | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the sovent. The material is allowed to cool and then packaged.

EXAMPLE 12

| Granule | |
|---|---|
| Methyl 4-[[(4-methoxy-6-methylpyrimidin-2-yl)-aminocarbonyl]aminosulfonyl]-3-isothiazole-carboxylate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 13

| Low Strength Granule | |
|---|---|
| Methyl 4-[[(4-methoxy-6-methylpyrimidin-2-yl)-aminocarbonyl]aminosulfonyl]-3-isothiazole-carboxylate | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then granules are packaged.

EXAMPLE 14

| Aqueous Suspension | |
|---|---|
| Methyl 4-[[(4,6-dimethoxypyrimidin-2-yl)aminocarbonyl]-aminosulfonyl]-3-isothiazolecarboxylate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| Methyl 4-[[(4,6-dimethoxypyrimidin-2-yl)aminocarbonyl]-aminosulfonyl]-3-isothiazolecarboxylate, sodium salt | 5% |
| water | 95% |

The salt is added directly to the water with stirring to producce the solution, which may then be packaged for use.

EXAMPLE 16

| High Strength Concentrate | |
|---|---|
| Methyl 4-[[(4-methoxy-6-methylpyrimidin-2-yl)-aminocarbonyl]aminosulfonyl]-3-isothiazole-carboxylate | 99% |
| silica aerogel | 0.5% |
| synthetic amorphous silica | 0.5% |

The ingredient are blended and ground in a hammer-mill to produce a material essentially all passing a U.S.S. No. 50 screen (0.3 mm opening). The concentrate may be formulated further if necessary.

EXAMPLE 17

| Wettable Powder | |
|---|---|
| Methyl 4-[[(4-methoxy-6-methylpyrimidin-2-yl)-aminocarbonyl]aminosulfonyl]-3-isothiazole-carboxylate | 90% |

-continued

| Wettable Powder | |
|---|---|
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

| Wettable Powder | |
|---|---|
| Methyl 4-[[(4,6-dimethoxypyrimidin-2-yl)aminocarbonyl]-aminosulfonyl]-3-isothiazolecarboxylate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

| Oil Suspension | |
|---|---|
| Methyl 4-[[(4-methoxy-6-methylpyrimidin-2-yl)-aminocarbonyl]aminosulfonyl]-3-isothiazole-carboxylate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 20

| Dust | |
|---|---|
| Methyl 4-[[(4,6-dimethoxypyrimidin-2-yl)aminocarbonyl]-aminosulfonyl]-3-isothiazolecarboxylate | 10% |
| attapulgite | 10% |
| pyrophyllite | 80% |

The active ingredient is blended with attapulgite and then passed through a hammer-mill to produce particles substantially all below 200 microns. The ground concentrate is then blended with powder pyrophyllite until homogenous.

EXAMPLE 21

| Oil Suspension | |
|---|---|
| Methyl 4-[[(4,6-dimethoxypyrimidin-2-yl)aminocarbonyl]-aminosulfonyl]-3-isothiazolecarboxylate | 25% |
| polyoxyethylene sorbitol hexaoleate | 5% |
| highly aliphatic hydrocarbon oil | 70% |

The ingredientss are ground together in a sand mill until the solid particles have been reduced to under about 5 microns. The resulting thick suspension may be applied directly, but preferably after being extended with oils or emulsified in water.

EXAMPLE 22

| Wettable Powder | |
|---|---|
| Methyl 4-[[(4-methoxy-6-methylpyrimidin-2-yl)-aminocarbonyl]aminosulfonyl]-3-isothiazole-carboxylate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

UTILITY

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, hgihway and railroad structures. Alternatively, many of the subject compounds should be useful for the selective pre- or post-emergence weed control in crops, such as wheat and barley.

The rates of application for the compounds of the invention are determined by a number of factors, including their use as selective or general herbicides, the crop species involved, the types of weeds to be controlled, weather and climate, formulations selected, mode of application, amount of foliage present, eyc. In general terms, the subject compounds should be applied at levels of around 0.125 to 10 kg/ha, the lower rates being suggested for use on lighter soils and/or those having a low organic matter content, for selective weed control or for situations where only short-term persistence is required. The compounds are applied to the locus of the plants to be controlled, i.e., to the soil in which seeds are planted for pre-emergence control or to the plants themselves for post-emergence control.

The compounds of the invention may be used in combinations with any other commercial herbicide examples of which are those of the triazine, triazole, uracil, urea, amide, diphenylether, carbamate and bipyridylium types.

The herbicidal properties of the subject compounds were dissolved in a number of greenhouse tests. The test procedures and results follow.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, sugar beet, rice, wheat and purple nutsedge (*Cyperus rotundus*) tubers were planted and treaated pre-emergence with the test chemicals dissolved in a nonphytoxic solvent. At the same time, these crop and weed species, alongg with cotton and bush bean, were treated with a soil/foliage application. At the same time of treatment, the plants ranged in height from 2 to 18 cm. Treated plants and controls were maintained in a greenhouse for sixteen days, after which all speceis were compared to controls and visually rated for response to treatment. The ratings, summarized in Table A, are based on a numerical scale extending from 0=no injury, to 10=complete kill. The accompanying descriptive symbols have the following meanings:
C=chlorosis/necrosis;
E=emergence inhibition;
G=growth retardation;
H=formative effect;
P=terminal bud kill;
S=albinism;
X=axillary stimulation; and
6Y=abscised buds or flowers.

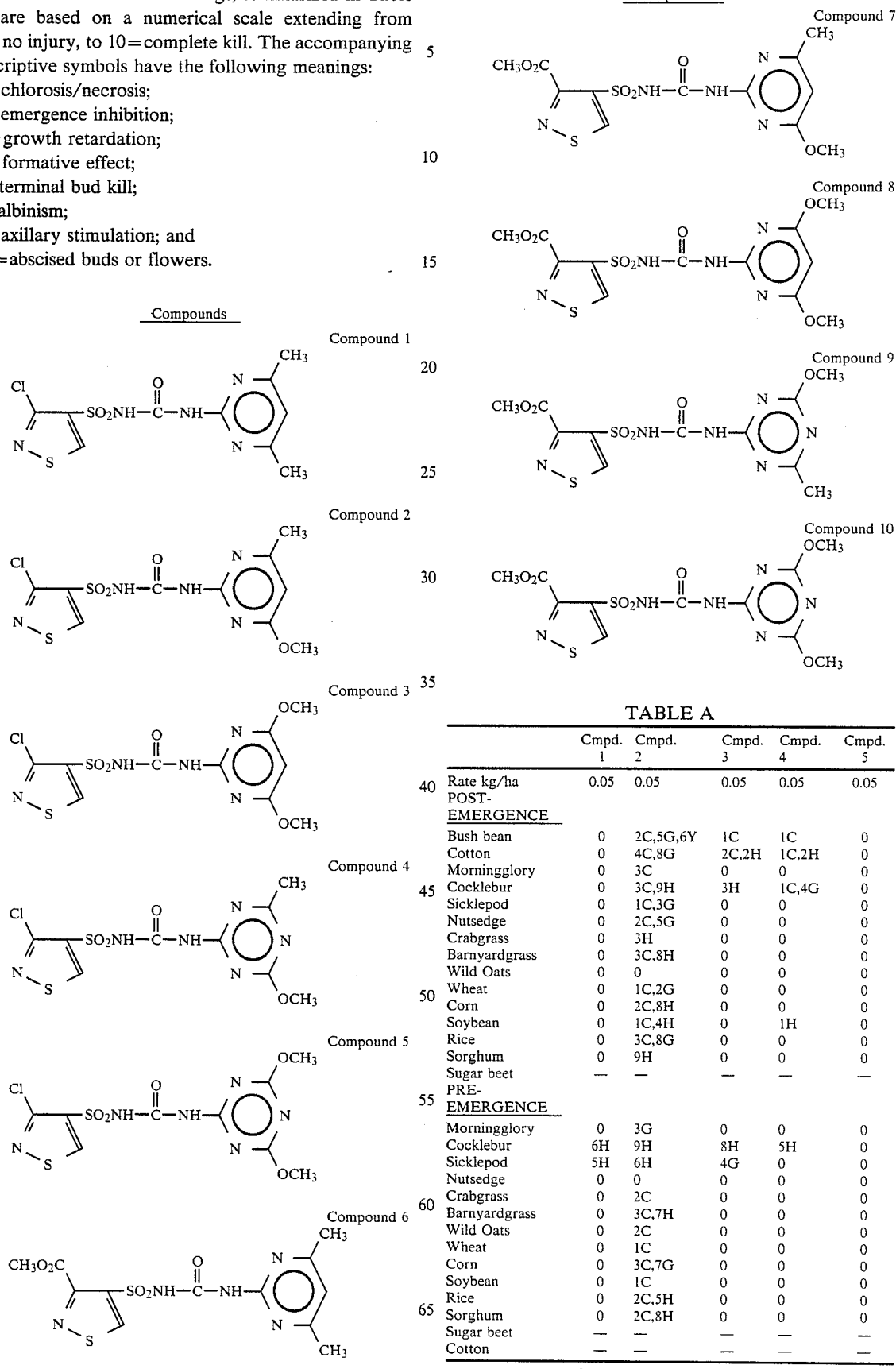

| | Cmpd. 1 | Cmpd. 2 | Cmpd. 3 | Cmpd. 4 | Cmpd. 5 |
|---|---|---|---|---|---|
| Rate kg/ha | 0.05 | 0.05 | 0.05 | 0.05 | 0.05 |
| POST-EMERGENCE | | | | | |
| Bush bean | 0 | 2C,5G,6Y | 1C | 1C | 0 |
| Cotton | 0 | 4C,8G | 2C,2H | 1C,2H | 0 |
| Morningglory | 0 | 3C | 0 | 0 | 0 |
| Cocklebur | 0 | 3C,9H | 3H | 1C,4G | 0 |
| Sicklepod | 0 | 1C,3G | 0 | 0 | 0 |
| Nutsedge | 0 | 2C,5G | 0 | 0 | 0 |
| Crabgrass | 0 | 3H | 0 | 0 | 0 |
| Barnyardgrass | 0 | 3C,8H | 0 | 0 | 0 |
| Wild Oats | 0 | 0 | 0 | 0 | 0 |
| Wheat | 0 | 1C,2G | 0 | 0 | 0 |
| Corn | 0 | 2C,8H | 0 | 0 | 0 |
| Soybean | 0 | 1C,4H | 0 | 1H | 0 |
| Rice | 0 | 3C,8G | 0 | 0 | 0 |
| Sorghum | 0 | 9H | 0 | 0 | 0 |
| Sugar beet | — | — | — | — | — |
| PRE-EMERGENCE | | | | | |
| Morningglory | 0 | 3G | 0 | 0 | 0 |
| Cocklebur | 6H | 9H | 8H | 5H | 0 |
| Sicklepod | 5H | 6H | 4G | 0 | 0 |
| Nutsedge | 0 | 0 | 0 | 0 | 0 |
| Crabgrass | 0 | 2C | 0 | 0 | 0 |
| Barnyardgrass | 0 | 3C,7H | 0 | 0 | 0 |
| Wild Oats | 0 | 2C | 0 | 0 | 0 |
| Wheat | 0 | 1C | 0 | 0 | 0 |
| Corn | 0 | 3C,7G | 0 | 0 | 0 |
| Soybean | 0 | 1C | 0 | 0 | 0 |
| Rice | 0 | 2C,5H | 0 | 0 | 0 |
| Sorghum | 0 | 2C,8H | 0 | 0 | 0 |
| Sugar beet | — | — | — | — | — |
| Cotton | — | — | — | — | — |
| | Cmpd. | Cmpd. | | Cmpd. | Cmpd. |

TABLE A-continued

| | 6 | 7 | 8 | 9 |
|---|---|---|---|---|
| Rate kg/ha | 0.05 | 0.05 | 0.05 | 0.05 |
| POST-EMERGENCE | | | | |
| Bush bean | 1C | 3C,3H,6Y | 2C,2G | 4C,8G,6Y |
| Cotton | 2C | 4C | 4C,8G | 4C |
| Morningglory | 2C,4H | 4C,6H | 3C,6G | 3C |
| Cocklebur | 4G | 2C,6G | 5C,9G | 4C,8G |
| Sicklepod | 0 | 0 | 0 | 2C |
| Nutsedge | 2G | 0 | 4G | 0 |
| Crabgrass | 0 | 0 | 2G | 0 |
| Barnyardgrass | 3H | 3C,8H | 3C,8H | 1C,1H |
| Wild Oats | 0 | 0 | 0 | 0 |
| Wheat | 0 | 0 | 0 | 0 |
| Corn | 2H | 2C,3H | 2H | 3H |
| Soybean | 0 | 3G | 1C,6G | 2G |
| Rice | 0 | 2C,7G | 1C,7G | 0 |
| Sorghum | 2C,8H | 2C,9G | 4C,9H | 0 |
| Sugar beet | 4C,9G | 4C,9G | 5C,9G | 5C,8G |
| PRE-EMERGENCE | | | | |
| Morningglory | 5C,7H | 9G | 9G | 3C,6H |
| Cocklebur | 6H | — | 9H | 5H |
| Sicklepod | 1C | 7H | 8G | 2C |
| Nutsedge | 0 | 0 | 3G | 0 |
| Crabgrass | 0 | 2G | 2G | 1C |
| Barnyardgrass | 0 | 4C,8H | 3C,8H | 1C |
| Wild Oats | 0 | 2C,6G | 3C,4G | 0 |
| Wheat | 0 | 8G | 2C,6G | 0 |
| Corn | 2C,5G | 2C,6G | 2C,6G | 2G |
| Soybean | 0 | 0 | 0 | 1C |
| Rice | 2C,6G | 9H | 10E | 2C,3G |
| Sorghum | 2C,8G | 9H | 3C,8H | 1C,4G |
| Sugar beet | 5C,9G | 5C,9G | 5C,9G | 3C,8G |
| Cotton | — | — | — | — |

| | Cmpd. 10 | Cmpd. 1 | Cmpd. 3 |
|---|---|---|---|
| Rate kg/ha | 0.05 | 0.4 | 0.4 |
| POST-EMERGENCE | | | |
| Bush bean | 2C,2H | 2C | 2C,5G |
| Cotton | 2C | 2C | 4C,8H |
| Morningglory | 3C | 3C | 2C,6G |
| Cocklebur | 0 | 3C,9G | 9C |
| Sicklepod | 0 | 1C | 1C,3G |
| Nutsedge | 0 | 0 | 3C,9G |
| Crabgrass | 0 | 2G | 1C |
| Barnyardgrass | 0 | 4H | 1H |
| Wild Oats | 0 | 0 | 0 |
| Wheat | 0 | 0 | 0 |
| Corn | 0 | 0 | 4G |
| Soybean | 0 | 1H | 1C,3H,5G |
| Rice | 0 | 2C,9G | 4C,9G |
| Sorghum | 5H | 2C,8H | 6H |
| Sugar beet | 4C,8G | — | — |
| PRE-EMERGENCE | | | |
| Morningglory | 2C,5H | 3G | 8G |
| Cocklebur | 0 | 8G | 9H |
| Sicklepod | 0 | 2C,5G | 2C,9G |
| Nutsedge | 0 | 0 | 9G |
| Crabgrass | 0 | 0 | 1C |
| Barnyardgrass | 2C | 2C | 6C |
| Wild Oats | 2C | 0 | 0 |
| Wheat | 2C | 2G | 2G |
| Corn | 0 | 2C,5G | 4C,7G |
| Soybean | 0 | 1C | 2C,6H |
| Rice | 1C | 2C,7H | 3C,8H |
| Sorghum | 5G | 2C | 3C,5H |
| Sugar beet | 3C,7G | — | — |
| Cotton | — | — | — |

| | Cmpd. 4 | Cmpd. 5 |
|---|---|---|
| Rate kg/ha | 0.4 | 0.4 |
| POST-EMERGENCE | | |
| Bush bean | 5C,8G,6Y | 1C,3G |
| Cotton | 2C,4G | 1H |
| Morningglory | 2C,8G | 2C |
| Cocklebur | 2C,9G | 2C |
| Sicklepod | 1C | 0 |
| Nutsedge | 0 | 0 |
| Crabgrass | 0 | 0 |
| Barnyardgrass | 0 | 0 |
| Wild Oats | 0 | 0 |
| Wheat | 0 | 0 |
| Corn | 1C,5G | 2G |
| Soybean | 4H | 2H |
| Rice | 1C,5G | 2H |
| Sorghum | 2C,5H | 1H |
| Sugar beet | — | — |
| PRE-EMERGENCE | | |
| Morningglory | 9G | 9G |
| Cocklebur | 9H,3C | 2H |
| Sicklepod | 6G | 2H |
| Nutsedge | 5G | 0 |
| Crabgrass | 1C | 0 |
| Barnyardgrass | 1C | 0 |
| Wild Oats | 0 | 0 |
| Wheat | 0 | 0 |
| Corn | 3C,7G | 1C,5G |
| Soybean | 1C | 1C |
| Rice | 3C,5G | 2C,5G |
| Sorghum | 1C,3G | 0 |
| Sugar beet | — | — |
| Cotton | — | — |

A test was performed according to the procedure described below to further define the activity of the claimed compounds as pre-emergence herbicides.

TEST B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederecea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for TEST A. The data for Compound 8 are summarized in Table B. Compound 2 was also tested and was shown to have activity as a pre-emergence treatment for the control of a number of species at rates as low as 0.03 kg/ha. Both of the compounds were safe on wheat at rates of 0.03 kg/ha (Compound 2) and 0.06 kg/ha (Compound 8).

TABLE B

| PRE-EMERGENCE ON WOODSTOWN SANDY LOAM | | |
|---|---|---|
| | Compound 8 | |
| Rate kg/ha | 0.06 | 0.250 |
| Crabgrass | 0 | 3G |
| Barnyardgrass | 4G | 8G |
| Sorghum | 5G | 8G,7H |
| Wild Oats | 0 | 3G |

TABLE B-continued

PRE-EMERGENCE ON WOODSTOWN SANDY LOAM

|  | Compound 8 | |
| --- | --- | --- |
| Johnsongrass | 2G | 4G |
| Dallisgrass | 0 | 2G |
| Giant foxtail | 2G | 7G |
| Ky. bluegrass | 0 | 0 |
| Cheatgrass | 5G | 9G |
| Sugar beets | 9G | 9G |
| Corn | 3G | 5G |
| Mustard | 8G | 9G,9C |
| Cocklebur | 7G | 9G |
| Nutsedge | 2G | 7G |
| Cotton | 2G | 8G |
| Morningglory | 5G | 8G |
| Sicklepd | 5G | 8G |
| Teaweed | 0 | 6G |
| Velvetleaf | 7G | 9G |
| Jimsonweed | 4G | 8G |
| Soybean | 0 | 2G |
| Rice | 6G | 10C |
| Wheat | 0 | 2G |

A test according to the following procedure was performed to better define the post-emergence utility of compounds of this invention.

TEST C

The test chemicals, dissolved in a non-phytoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and rape. All plants were sprayed approximately 14 days after planting. Additional plant species, such as johnsongrass and field bindweed, are sometimes added to this standard test in order to evaluate unusual selectivity.

Results for Compound 8 are presented in Table C, and it can be seen that this compound should be useful for the post-emergence control of weeds in wheat. Compounds 9 and 10 showed comparable control of the tested weed species and relative safety to wheat.

TABLE C

| Over-the-Top Soil/Foliage Treatment | | |
| --- | --- | --- |
|  | Compound 8 | |
| Rate kg/ha | 0.015 | 0.06 |
| Soybeans | 9G | 10C |
| Velvetleaf | 7G,6C | 8G,7C |

TABLE C-continued

| Over-the-Top Soil/Foliage Treatment | | |
| --- | --- | --- |
|  | Compound 8 | |
| Sesbania | 9G | 10C |
| Sicklepod | 5G | 7G |
| Cotton | 9G | 9G |
| Morningglory | 8G | 8G |
| Alfalfa | 2G,1C | 3G,2C |
| Jimsonweed | 1G | 6G |
| Cocklebur | 6G | 8G |
| Sunflower | 9G | 9G |
| Rape | 7G | 7G |
| Sugar beets | 10C | 10C |
| Corn | 4H,5G | 8G,7C |
| Crabgrass | 6G | 6G |
| Rice | 7G,4C | 7G,5C |
| Nutsedge | 4G | 5G |
| Barnyardgrass | 4G | 9G,7C |
| Wheat | 0 | 2G |
| Giant foxtail | 4G | 8G,7C |
| Wild Oats | 0 | 1G |
| Sorghum | 4G | 8G |
| Johnsongrass | 4G | 2G,5C |
| Field Bindweed | 4G | 6G |

What is claimed is:

1. A compound of the formula:

where
Q is

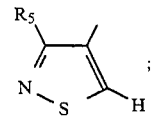

$R_5$ is Cl, $C_1$–$C_3$ alkoxycarbonyl or $C_1$–$C_3$ alkyl;
A is

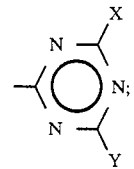

X is $CH_3$, $OCH_3$, $OC_2H_5$, $CH_2OCH_3$, or cyclopropyl; and
Y is $CH_3$, $OCH_3$, or
and agriculturally suitable salts thereof.

2. A compound of claim 1 where X is $CH_3$, $OCH_3$, $OC_2H_5$ or $CH_2OCH_3$.

3. An agricultural composition comprising an herbicidally effective amount of a compound of claim 1 and at least one of the following: (a) a surfactant and (b) a solid or liquid diluent.

4. An agricultural composition comprising an herbicidally effective amount of a compound of claim 2 and at least one of the following: (a) a surfactant and (b) a solid or liquid diluent.

5. A method for controlling the growth of undesired vegetation comprising applying to the locus of such vegetation an agriculturally effective amount of a compound of claim 1.

6. A method for controlling the growth of undesired vegetation comprrising applying to the locus of such vegetation an agriculturally effective amount of a compound of claim 2.

* * * * *